US007390771B2

(12) United States Patent
Kawakami et al.

(10) Patent No.: US 7,390,771 B2
(45) Date of Patent: Jun. 24, 2008

(54) RECORDING MATERIAL AND RECORDING SHEET

(75) Inventors: Tadashi Kawakami, Ichihara (JP); Shinichi Sato, Ichihara (JP); Hiroshi Fujii, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 463 days.

(21) Appl. No.: 10/999,630

(22) Filed: Nov. 30, 2004

(65) Prior Publication Data

US 2005/0148468 A1 Jul. 7, 2005

Related U.S. Application Data

(63) Continuation-in-part of application No. 10/472,125, filed on Sep. 16, 2003, now abandoned, which is a continuation-in-part of application No. PCT/JP03/06818, filed on May 30, 2003.

(30) Foreign Application Priority Data

| | | |
|---|---|---|
| Jun. 3, 2002 | (JP) | 2002-162055 |
| Jun. 3, 2002 | (JP) | 2002-162058 |
| Aug. 5, 2002 | (JP) | 2002-227021 |
| Sep. 25, 2002 | (JP) | 2002-278780 |
| Oct. 9, 2002 | (JP) | 2002-295706 |
| Dec. 9, 2002 | (JP) | 2002-356280 |
| Dec. 19, 2002 | (JP) | 2002-367645 |
| Feb. 4, 2003 | (JP) | 2003-026674 |
| Feb. 4, 2003 | (JP) | 2003-027583 |
| Apr. 10, 2003 | (JP) | 2003-106234 |

(51) Int. Cl.
*B41M 5/20* (2006.01)
*C07C 303/00* (2006.01)

(52) U.S. Cl. .......... 503/216; 564/80

(58) Field of Classification Search .......... 503/216; 564/80

See application file for complete search history.

(56) References Cited

U.S. PATENT DOCUMENTS 4,075,227 A 2/1978 Jones et al.

FOREIGN PATENT DOCUMENTS

| | | |
|---|---|---|
| AU | 7555500 | 5/2001 |
| JP | 63-153182 | 6/1988 |
| JP | 2-293195 | 12/1990 |
| JP | 3-293195 | 12/1991 |
| JP | 2001-288163 | 10/2001 |
| JP | 2002-113951 | 4/2002 |
| JP | 2002-137554 | 5/2002 |
| JP | 2002-264538 | 9/2002 |
| JP | 2002-301873 | 10/2002 |
| WO | WO 01/25193 A1 | 4/2001 |
| WO | WO-02/081229 A1 | 10/2002 |
| WO | WO-03/101751 A1 | 12/2003 |

OTHER PUBLICATIONS

Hamada et al., 2004, CAS: 141:44912.*

* cited by examiner

*Primary Examiner*—Rei-Tsang Shiao
(74) *Attorney, Agent, or Firm*—Darby & Darby P.C.

(57) ABSTRACT

The present invention provides a composition and a recording material made from the composition having an excellent dynamic sensitivity in recording as well as an excellent image stability and, particularly, having excellent resistance for heat and humidity, heat, light, plasticizer and water. The composition and the recording material include the following compounds (1), (2), and (3):

(1)

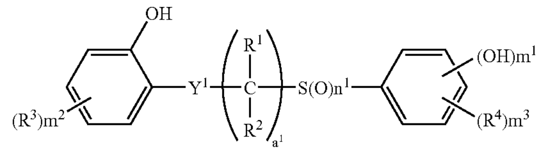

(2)

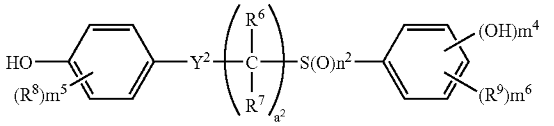

(3)

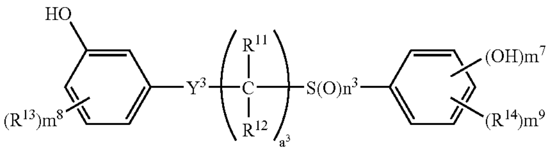

wherein $R^1$, $R^2$, $R^6$, $R^7$, $R^{11}$, and $R^{12}$ each represents hydrogen or an alkyl group; $a^1$ to $a^3$ each represents an integer of 1-6; $n^1$ to $n^3$ each represents 0, 1 or 2; $m^1$, $m^4$ and $m^7$ each represents 0, 1, 2 or 3; $R^3$, $R^4$, $R^8$, $R^9$, $R^{13}$ and $R^{14}$ each represents an alkyl group; $m^2$, $m^3$, $m^5$, $m^6$, $m^8$ and $m^9$ each represents 0, 1 or 2; and $Y^1$ to $Y^3$ each represents CO or NRCO (R represents hydrogen, etc.).

7 Claims, No Drawings

RECORDING MATERIAL AND RECORDING SHEET

CROSS REFERENCE TO RELATED APPLICATION

This is a continuation-in-part of U.S. application Ser. No. 10/472,125, filed Sep. 16, 2003, now abandoned, which claims the benefit of International Application Number PCT/JP02/03159, filed Mar. 29, 2002, and a continuation-in-part of International Application Number PCT/JP03/06818, filed May 30, 2003.

TECHNICAL FIELD OF INVENTION

The present invention relates to a composition having an excellent dynamic sensitivity in recording as well as an excellent image stability and, particularly, having excellent resistance for heat and humidity, heat, light, plasticizer and water, relates to a recording material made from the composition and relates to a recording sheet comprising a base sheet and a recording material layer made from the recording material on the base sheet.

BACKGROUND ART

A recording material making use of color development based on a chemical reaction between a color forming dye and a developer is capable of carrying out a recording process in a relatively simple apparatus and within a short period of time without performing complicated processing such as development fixing. Thus, such recording material is used in a wide range of applications including pressuresensitive copying materials or thermal recording materials of output-recording units employed in facsimile machines or printers.

The capability to develop colors quickly and maintain the whiteness of the portion with no developed colors is demanded of these recording materials. The portion with no developed colors is hereafter referred to as the background. In addition, high durability of background and image is demanded of these recording materials. In recent years, particularly, a large amount of recording material is being used in a field where the reliability of a recorded image is considered to be of high importance. As a result, there is an increase in the demand for a recording material having an excellent image stability such as heat and humidity, heat, light, water and plasticizer (included in a macromolecular material) resistance.

With one kind of developer, however, it is difficult to provide a recording material satisfying all the demands described above. In addition, while attempts have been made to use a mixture consisting of a developer exhibiting a good heat and humidity resistance and a developer having a good light resistance, a recording material that sufficiently satisfies all the requirements has not yet been invented. As described earlier, the requirements include an excellent sensitivity in recording, heat and humidity, heat, light, plasticizer and water resistance. When a recording material does not satisfy all the requirements, a phenomenon called background fogging typically occurs after the creation of a piece of thermal recording paper. A background fogging is a phenomenon in which color is generated on the thermal recording paper.

DISCLOSURE OF THE INVENTION

In accordance with a first aspect of the present invention, there is provided a composition including:

at least one type of a compound represented by Formula (1); wherein (1)

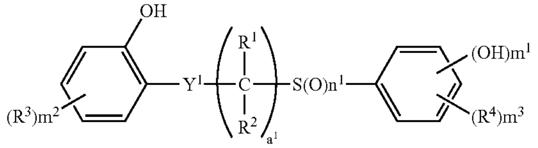

$R^1$ and $R^2$ each independently represent hydrogen or C1-C6 alkyl, $a^1$ represents an integer of 1 to 6, $n^1$ represents 0, 1 or 2, $m^1$ represents 0 or an integer in the range 1 to 3, $R^3$ and $R^4$ each independently represent nitro, carboxyl, halogen, C1-C6 alkyl or C2-C6 alkenyl, $m^2$ and $m^3$ each independently represent 0, 1 or 2;

$R^3$ and $R^4$ may be different to each other when $m^2$ and $m^3$ represent each 2, $Y^1$ represents CO or $NR^5CO$ (in the equation, $R^5$ represents hydrogen or C1-C6 alkyl);

at least one type of a compound represented by Formula (2); wherein (2)

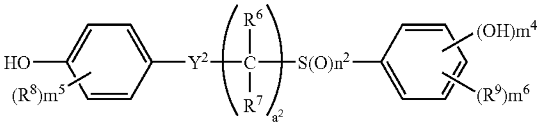

$R^6$ and $R^7$ each independently represent hydrogen or C1-C6 alkyl, $a^2$ represents an integer of 1 to 6, $n^2$ represents 0, 1 or 2, $m^4$ represents 0 or an integer in the range 1 to 3, $R^8$ and $R^9$ each independently represent nitro, carboxyl, halogen, C1-C6 alkyl or C2-C6 alkenyl, $m^5$ and $m^6$ each independently represent 0, 1 or 2;

$R^8$ and $R^9$ may be different to each other when $m^5$ and m represent each 2, $Y^2$ represents CO or $NR^{10}CO$ (in the equation, $R^{10}$ represents hydrogen or C1-C6 alkyl); and/or at least one type of a compound represented by Formula (3); wherein (3)

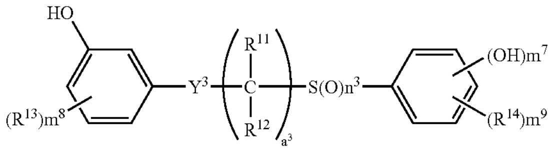

$R^{11}$ and $R^{12}$ each independently represent hydrogen or C1-C6 alkyl, $a^3$ represents an integer of 1 to 6, $n^3$ represents 0, 1 or 2, $m^7$ represents 0 or an integer in the range 1 to 3, $R^{13}$ and $R^{14}$ each independently represent nitro, carboxyl, halogen, C1-C6 alkyl or C2-C6 alkenyl, $m^8$ and $m^9$ each independently represent 0, 1 or 2;

$R^{13}$ and $R^{14}$ may be different to each other when $m^8$ and $m^9$ represent each 2, $Y^3$ represents CO or $NR^{15}CO$ (in the equation, $R^{15}$ represents hydrogen or C1-C6 alkyl);

In accordance with a second aspect of the present invention, there is provided a recording material including at least one type of the compound represented by the said Formula (1), at least one type of the compound represented by the said Formula (2) and/or at least one type of the compound represented by the said Formula (3).

It is desirable to provide the recording material according to the second aspect of the present invention wherein the compound represented by the said Formula (2) and/or the compound represented by the said Formula (3) each have a content quantity in the range 5 to 500 parts by weight relative to 100 parts by weight of the compound represented by the said Formula (1).

In accordance with a third aspect of the present invention, there is provided a recording sheet comprising a base sheet and a recording material layer made from the recording material according to the second aspect of the present invention on the said base sheet.

The recording material layer made from the recording material according to the second aspect of the present invention has an excellent dynamic sensitivity in recording as well as an excellent image stability and, particularly, has excellent property such as heat and humidity, heat, light, plasticizer and water resistance. In addition, there is no generation of the background fogging phenomenon, which is commonly observed in conventional methods that use a mixture of the developers. In the present invention, dynamic sensitivity is defined as a sensitivity obtained as a optical density measured by instantaneously applying thermal energy generated by a thermal head (employed in a thermal printer) in the form of an ordinary pulse having a duration in the range 0.2 to 1.8 msec to a piece of thermal recording paper.

As described above, the composition provided by the present invention comprises at least one type of the compound represented by the said Formula (1), at least one type of the compound represented by the said Formula (2) and/or at least one type of the compound represented by the said Formula (3). While the weight ratios among the compounds are arbitrary, the compound represented by the said Formula (2) and/or the compound represented by the said Formula (3) normally each have a content quantity in the range 5 to 500 parts by weight relative to 100 parts by weight of the compound represented by the said Formula (1). It is desirable, however, to adjust the weight ratios so that the compound represented by the said Formula (2) and/or the compound represented by the said Formula (3) each have a content quantity in the range 10 to 300 parts by weight relative to 100 parts by weight of the compound represented by the said Formula (1). It is even more desirable to adjust the weight ratios so that the compound represented by the said Formula (2) and/or the compound represented by the said Formula (3) each have a content quantity in the range 20 to 250 parts by weight relative to 100 parts by weight of the compound represented by the said Formula (1).

The compounds represented by the said Formula (1), wherein the portion of $S(O)n^1$ is S, to be used in the present invention can be obtained by the reaction of the compound represented by Formula (4);

(4)

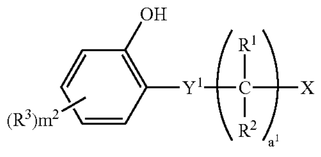

wherein $R^1$, $R^2$, $R^3$, $Y^1$, $a^1$ and $m^2$ each have the same meaning as the one previously described, and X represents halogen, such as a chlorine or bromine, with a compound represented by Formula (5);

(5)

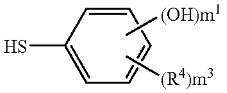

wherein $R^4$, $m^1$ and $m^3$ each have the same meaning as the one previously described, in an organic solvent such as methanol with the presence of a base such as a potassium hydroxide.

Compounds represented by the said Formula (1), wherein the portion of $S(O)n^1$ is SO or $SO_2$, may be obtained by oxidizing the compound obtained by the reaction herein above with an oxidizing agent, such as aqueous solution of hydrogen peroxide and m-chloroperbenzoic acid in an organic solvent such as acetic acid.

Compounds represented by the said Formula (4), wherein the portion of $Y^1$ is $NR^5CO$, can be obtained by the reaction of the compound represented by Formula (6);

(6)

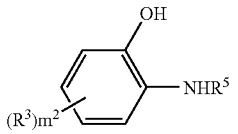

wherein $R^3$, $R^5$ and $m^2$ each have the same meaning as the one previously described, with the compound represented by Formula (7);

(7)

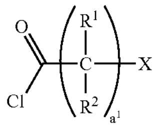

wherein $R^1$, $R^2$, X and $a^1$ each have the same meaning as the one previously described, in an organic solvent such as acetonitrile, and water with the presence of a base such as potassium bicarbonate.

Compounds represented by the said Formula (4), wherein the portion of Y is CO, can be obtained by the reaction of the compound represented by Formula (8);

(8)

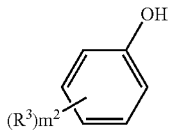

wherein $R^3$ and $m^2$ each have the same meaning as the one previously described, with a compound represented by the said Formula (7), in an organic solvent such as dichloromethane with the presence of a Lewis acid such as aluminum chloride.

A compound represented by the said Formula (2) and a compound represented by the said Formula (3) can each be synthesized in the same way as a compound represented by the said Formula (1).

As methods of mixing a compound represented by Formula (1) with a compound(s) represented by Formulas (2) and/or (3), it is possible to adopt a method of mixing powders of the compounds, a fusion-mixing method, a method of adding and mixing of the compounds during crystallization of the compound represented by Formula (1) and a method of having a chemical reaction using a mixture such as o-hydroxyaniline, m-hydroxyaniline or p-hydroxyaniline as hydroxyaniline of the raw materials and synthesizing/including compounds of at least two or three types at the same time.

In Formula (1), $R^1$ and $R^2$ each independently represent hydrogen; C1-C6 alkyl such as methyl, ethyl, n-propyl, isopropyl, n-butyl and tert-butyl.

$a^1$ represents an integer of 1 to 6;

$n^1$ represents 0, 1 or 2;

$m^1$ represents 0 or an integer of 1 to 3.

$R^3$ and $R^4$ each independently represent nitro; carboxyl; halogen such as fluorine, chlorine, bromine and iodine; C1-C6 alkyl such as methyl, ethyl, n-propyl, isopropyl, n-butyl and tert-butyl; C2-C6 alkenyl such as propenyl, isopropenyl and butenyl.

$m^2$ and $m^3$ each independently represent 0, 1 or 2, and $Y^1$ represents CO or $NR^5CO$.

$R^5$ represents hydrogen; C1-C6 alkyl such as methyl, ethyl, n-propyl, isopropyl, n-butyl and tert-butyl.

Compounds represented by Formula (1) particularly include a preferred compound in which $Y^1$ represents $NR^5CO$ and a more preferred compound in which $Y^1$ represents NHCO. Examples of compounds represented by Formula (1) are N-(2'-hydroxyphenylthio)acetyl-2-hydroxyaniline, N-(3'-hydroxyphenylthio)acetyl-2-hydroxyaniline, N-(4'-hydroxyphenylthio)acetyl-2-hydroxyaniline and the like.

Another recording material provided by the present invention includes at least one type of the compound represented by Formula (2) and at least one type of the compound represented by Formula (3).

In Formula (2), $R^6$ and $R^7$ each independently represent hydrogen; C1-C6 alkyl such as methyl, ethyl, n-propyl, isopropyl, n-butyl and tert-butyl.

$a^2$ represents an integer of 1 to 6, and $n^2$ represents 0, 1 or 2.

$m^4$ represents 0 or an integer of 1 to 3.

$R^8$ and $R^9$ each independently represent nitro; carboxyl; halogen such as fluorine, chlorine, bromine and iodine; C1-C6 alkyl such as methyl, ethyl, n-propyl, isopropyl, n-butyl and tert-butyl; C2-C6 alkenyl such as propenyl, isopropenyl and butenyl.

$m^5$ and $m^6$ each independently represent 0, 1 or 2, and $Y^2$ represents CO or $NR^{10}CO$.

$R^{10}$ represents hydrogen; C1-C6 alkyl, such as methyl, ethyl, n-propyl, isopropyl, n-butyl and tert-butyl.

Compounds represented by Formula (2) particularly include a preferred compound in which $Y^2$ represents $NR^{10}CO$ and a more preferred compound in which $Y^2$ represents NHCO.

Examples of the compounds represented by Formula (2) are the N-(2'-hydroxy phenyl thio)acetyl-4-hydroxy aniline, the N-(3'-hydroxy phenyl thio)acetyl-4-hydroxy aniline, the N-(4'-hydroxy phenyl thio)acetyl-4-hydroxy aniline and the like.

In Formula (3), $R^{11}$ and $R^{12}$ each independently represent hydrogen; C1-C6 alkyl such as methyl, ethyl, n-propyl, isopropyl, n-butyl and tert-butyl.

$a^3$ represents an integer of 1 to 6, and $n^3$ represents 0, 1 or 2, and $m^7$ represents 0 or an integer of 1 to 3.

$R^{13}$ and $R^{14}$ each independently represent nitro; carboxyl; halogen such as fluorine, chlorine, bromine and iodine; C1-C6 alkyl such as methyl, ethyl, n-propyl, isopropyl, n-butyl and tert-butyl; C2-C6 alkenyl such as propenyl, isopropenyl and butenyl.

$m^8$ and $m^9$ each independently represent 0, 1 or 2, and $Y^3$ represents CO or $NR^{15}CO$.

$R^{15}$ represents hydrogen; C1-C6 alkyl such as methyl, ethyl, n-propyl, isopropyl, n-butyl and tert-butyl.

Compounds represented by Formula (3) particularly include a preferred compound in which $Y^3$ represents $NR^{15}CO$ and a more preferred compound in which $Y^3$ represents NHCO.

Examples of the compounds represented by Formula (3) are the N-(2'-hydroxy phenyl thio)acetyl-3-hydroxy aniline, the N-(3'-hydroxy phenyl thio)acetyl-3-hydroxy aniline, the N-(4'-hydroxy phenyl thio)acetyl-3-hydroxy aniline and the like.

Preferred examples of the composition comprising a compound represented by the said Formula (1) and a compound represented by the said Formula (2) and/or (3) are items (a) to (c) listed as follows.

(a) N-(4'-hydroxyphenylthio)acetyl-2-hydroxyaniline and N-(4'-hydroxyphenylthio)acetyl-4-hydroxyaniline.

(b) N-(4'-hydroxyphenylthio)acetyl-2-hydroxyaniline and N-(4'-hydroxyphenylthio)acetyl-3-hydroxyaniline.

(c) N-(4'-hydroxyphenylthio)acetyl-2-hydroxyaniline, N-(4'-hydroxyphenylthio)acetyl-4-hydroxyaniline and N-(4'-hydroxyphenylthio)acetyl-3-hydroxyaniline.

The recording material provided by the present invention includes at least one type of a color forming dye and a compound represented by the said Formula (1) in addition to compounds represented by the said Formula (2) and/or Formula (3). That is to say, the recording material provided by the present invention may include both compounds represented by the said Formula (2) and Formula (3) or include only a compound represented by either the said Formula (2) or Formula (3).

In the recording material provided by the present invention, the compound represented by Formula (1) normally has a content quantity in the range 10 to 500 parts by weight relative to 100 parts by weight of the color forming dye. It is desirable, however, to adjust the weight ratio so that the compound represented by Formula (1) has a content quantity in the range 50 to 300 parts by weight relative to 100 parts by weight of the color forming dye. It is even more desirable to adjust the weight ratio so that the compound represented by Formula (1) has a content quantity in the range 50 to 200 parts by weight relative to 100 parts by weight of the color forming dye. If the compound represented by Formula (1) has a relative content quantity of 10 parts by weight or smaller, a sufficient saturated density will not be achieved. If the compound represented by Formula (1) has a relative content quantity greater than 500 parts by weight, on the other hand, the general content quantity of the developer is considered to be excessively large even though there is no conceivable bad effect in particular. An excessively large content quantity is not desirable because such a content quantity raises the cost of the thermal recording paper.

In addition, the compound represented by Formula (2) and the compound represented by Formula (3) normally have a total content quantity in the range 5 to 500 parts by weight relative to 100 parts by weight of the compound represented by Formula (1). It is desirable, however, to adjust the weight ratios so that the compound represented by Formula (2) and the compound represented by Formula (3) have a total content quantity in the range 10 to 300 parts by weight relative to 100 parts by weight of the compound represented by Formula (1). It is even more desirable to adjust the weight ratios so that the compound represented by Formula (2) and the compound represented by Formula (3) have a total content quantity in the range 20 to 250 parts by weight relative to 100 parts by weight of the compound represented by Formula (1). If the compound represented by Formula (2) and the compound represented by Formula (3) have a total relative content quantity of 5 parts by weight or smaller, it is feared that the heat and humidity resistance and plasticizer resistance of the image will deteriorate. If the compound represented by Formula (2) and the compound represented by Formula (3) have a total relative content quantity greater than 500 parts by weight, on the other hand, it is feared that the light resistance of the image will deteriorate.

In addition, the compound represented by Formula (1) and the compound represented by Formula (2) and/or the compound represented by Formula (3) normally have a total content quantity in the range 100 to 1,000 parts by weight relative to 100 parts by weight of the color forming dye. It is desirable, however, to adjust the weight ratios so that the compound represented by Formula (1) and the compound represented by Formula (2) and/or the compound represented by Formula (3) normally have a total content quantity in the range 150 to 500 parts by weight relative to 100 parts by weight of the color forming dye.

The composition and recording material of the present invention may include same compounds of a different degree of crystallinity as well as a variable crystalline form, those in an amorphous state and an adduct of the solvent. By properly selecting and using compounds with different crystalline forms, the background and sensitivity of the recording material can probably be improved. In addition, if the particle diameter of the compounds in a coating solution is made smaller, the sensitivity may be improved. In particular, the substance having a high degree of crystallinity results in a background with excellent brightness and an excellent heat resistance in comparison with a substance put in an amorphous state.

Methods of mixing the compound represented by the said Formula (1) and the compound represented by the said Formula (2) and/or the compound represented by the said Formula (3) include a method of mixing particles of the compounds, an additive method implemented during liquid mixture adjustment/dispersion time and an additive method implemented in a state of an dispersion. In addition, by selecting a process to produce compounds, a mixture of the compound represented by the said Formula (1) and the compound represented by the said Formula (2) and/or the compound represented by the said Formula (3) can be obtained in the process and used as it is.

The recording material of the present invention may also contain one or more of a known developer, an image stabilizer, an antioxidant, a desensitizer, an antitack agent, an antifoamer, a photo stabilizer and a fluorescent dye. These additional agents may be contained either in the color forming layer, or in an arbitrary layer, for example a protecting layer when the recording material is configured by a multi-layer structure. In particular, in the case of a structure including an overcoat layer and an undercoat layer respectively over and under the color forming layer, an antioxidant and a photo stabilizer may be included in the overcoat and undercoat layers by being contained in microcapsules if necessary.

Examples of the color forming dye used for the recording material of the present invention include leuco dyes based on fluoran, phthalide, lactam, triphenyl methane, fenothiazine, and spiropyran. However, the color forming dyes are not limited to these leuco dyes, and any color forming dyes may be used as far as it forms color by contacting with a developer of an acidic substance.

Examples of the color forming dyes based on fluoran include 3-diethylamino-6-methyl-7-anilino fluoran,
3-dibutylamino-6-methyl-7-anilinofluoran,
3-(N-ethyl-N-isobutylamino)-6-methyl-7-anilinofluoran,
3-(N-methyl-N-propylamino)-6-methyl-7-anilino fluoran,
3-(N-ethyl-N-isopentylamino)-6-methyl-7-anilinofluoran,
3-diethylamino-7-(o-chloroanilino)fluoran,
3-dibutylamino-7-(o-chloroanilino) fluoran
3-(N-ethyl-p-toluidino)-6-methyl-7-anilinofluoran,
3-(N-cyclohexyl-N-methylamino)-6-methyl-7-anilinofluoran,
3-pyrrolidino-6-methyl-7-anilinofluoran,
3-piperidino-6-methyl-7-anilinofluoran,
3-dimethylamino-7-(m-trifluoromethylanilino)fluoran,
3-dipentylamino-6-methyl-7-anilinofluoran,
3-(N-ethoxypropyl-N-ethylamino)-6-methyl-7-anilinofluoran,
3-dibutylamino-7-(o-fluoroanilino)fluoran,
3-diethylaminobenzo[a]fluoran,
3-dimethylamino-6-methyl-7-chlorofluoran,
3-diethylamino-5-methyl-7-dibenzylaminofluoran,
3-diethylamino-7-dibenzylaminofluoran,
3-diethylamino-5-chlorofluoran,
3-diethylamino-6-(N,N'-dibenzylamino)fluoran,
3,6-dimethoxyfluoran,
and 2, 4-dimethyl-6-(4-dimethylaminophenyl)aminofluoran.

Examples of the color forming dyes based on phthalide include 3-{4-[4-(4-anilino)-anilino]anilino}-6-methyl-7-chlorofluoran,
3,3-bis[2-(4-dimethylaminophenyl)-2-(4-methoxyphenyl) vinyl]-4,5,6,7-tetrachlorophthalide,
3,6,6'-tris(dimethylamino)spiro(fluorine-9,3'-phthalide),
and 3,3-bis(4'-dimethylaminophenyl)-6-diethylaminophthalide.

In particular, it is desirable to use color forming dyes pertaining to fluoran such as 3-diethylamino-6-methyl-7-anilinofluoran,
3-dibutylamino-6-methyl-7-anilinofluoran,
3-(N-ethyl-N-isobutylamino)-6-methyl-7-anilinofluoran,
3-(N-methyl-N-propylamino)-6-methyl-7-anilinofluoran,
3-(N-ethyl-N-isopentylamino)-6-methyl-7-anilinofluoran,
3-diethylamino-7-(6-chloroanilino)fluoran,
3-dibutylamino-7-(o-chloroanilino)fluoran,
3-(N-ethyl-p-toluidino)-6-methyl-7-anilinofluoran, 3-(N-cyclohexyl-N-methylamino)-6-methyl-7-anilinofluoran,
3-pyrrolidino-6-methyl-7-anilinofluoran,
3-piperidino-6-methyl-7-anilinofluoran,
3-dimethylamino-7-(m-trifluoromethylanilino)fluoran,
3-dipentylamino-6-methyl-7-anilinofluoran,
3-(N-ethoxypropyl-N-ethylamino)-6-methyl-7-anilinofluoran,
3-dibutylamino-7-(o-fluoroanilino)fluoran,
3-diethylaminobenzo[a]fluoran,
3-dimethylamino-6-methyl-7-chlorofluoran,
3-diethylamino-5-methyl-7-dibenzylaminofluoran,
3-diethylamino-7-dibenzylaminofluoran,
3-diethylamino-5-chlorofluoran,
3-diethylamino-6-(N,N'-dibenzylamino)fluoran,
3,6-dimethoxyfluoran and 2,4-dimethyl-6-(4-dimethylaminophenyl)aminofluoran.

It is even more desirable to use color forming dyes pertaining to fluoran such as 3-diethylamino-6-methyl-7-anilinofluoran,
3-dibutylamino-6-methyl-7-anilinofluoran,
3-(N-ethyl-N-isobutylamino)-6-methyl-7-anilinofluoran,
3-(N-methyl-N-propylamino)-6-methyl-7-anilinofluoran,
3-(N-ethyl-N-isopentylamino)-6-methyl-7-anilinofluoran and 3-(N-cyclohexyl-N-methylamino)-6-methyl-7-anilinofluoran.

Of course, these color forming dyes can each be used alone to give a recording material of a color developed by the dye, or two or more types of color forming dye can be mixed with each other. For example, it is possible to mix the color forming dyes of the elementary colors, namely, red, green and blue, or a black dye to make a recording material develop the truly black color. Other developers include those for thermal recording materials and those for pressuresensitive recording materials. Examples for the developer of thermal recording materials include bisphenol compounds, such as bisphenol A,
4,4'-sec-butylidenbisphenol,
4,4'-cyclohexylidenbisphenol,
2,2-dimethyl-3,3-bis(4-hydroxyphenyl)butane,
2,2'-dihydroxydiphenyl,
pentamethylene-bis(4-hydroxybenzoate),
2,2-dimethyl-3,3-di(4-hydroxyphenyl)pentane,
2,2-di(4-hydroxyphenyl)hexane;
sulfur-containing bisphenol compounds, such as 4,4'-dihydroxydiphenylthio ether,
1 ,7-di(4-hydroxyphenylthio)-3,5-dioxaheptane,
2,2'-bis(4-hydroxyphenylthio)diethyl ether,
4,4'-dihydroxy-3,3'-dimethyldiphenylthio ether;
4-hydroxybenzoic esters, such as benzyl 4-hydroxybenzoate,
ethyl 4-hydroxybenzoate,
propyl 4-hydroxybenzoate,
isopropyl 4-hydroxybenzoate,
butyl 4-hydroxybenzoate,
isobutyl 4-hydroxybenzoate,
chlorobenzyl 4-hydroxybenzoate,
methylbenzyl 4-hydroxybenzoate and diphenylmethyl 4-hydroxybenzoate;
metal salts of benzoic acid, such as zinc benzoate and zinc 4-nitrobenzoate;
salicylic acids, such as 4-[2-(4-methoxyphenyloxy)ethyloxy] salicylic acid;
metal salts of salicylic acid, such as zinc salicylate and bis[4-(octyloxycarbonylamino)-2-hydroxybenzoic acid] zinc;
hydroxysulfones, such as
4,4'-dihydroxydiphenylsulfone,
2,4'-dihydroxydiphenylsulfone,
4-hydroxy4'-methyldiphenylsulfone,
4-hydroxy-4'-isopropoxydiphenylsulfone,
4-hydroxy-4'-butoxydiphenylsulfone,
4,4'-dihydroxy-3,3'-diallyldiphenylsulfone,
3,4-dihydroxy-4'-methyldiphenylsulfone,
4,4'-dihydroxy-3,3',5,5'-tetrabromodiphenylsulfone;
4-hydroxyphthalic diesters, such as dimethyl 4-hydroxyphthalate,
dicyclohexyl 4-hydroxyphthalate and diphenyl 4-hydroxyphthalate;
hydroxynaphtoic esters, such as 2-hydroxy-6-carboxynaphthalene;
trihalomethylsulfones, such as tribromomethylphenylsulfone;
sulfonylureas, such as 4,4'-bis(p-toluenesulfonylaminocarbonylamino)diphenylmethane;
tetracyanoqinodimethanes; hydroxyacetophenone; p-phenylphenol;
benzyl 4-hydroxyphenylacetate; p-benzylphenol; hydroquinonemonobenzyl ether;
2,4-dihydroxy-2'-methoxydibenzanilide; and
diphenylsulfone bridged compounds represented by Formula (9) given below;

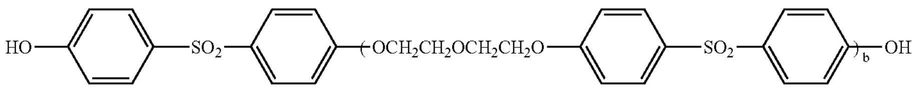
(9)

wherein b is an integer of 0 to 6, and mixtures of the compounds described above And examples of the developer for pressure-sensitive recording materials are:
inorganic acids, such as acid clay,
attapulgite,
activated clay,
bentonite,
colloidal silica,
aluminum silicate,
magnesium silicate,
zinc silicate,
tin silicate,
burned kaolin and talc;
aliphatic carboxylic acids, such as oxalic acid,
maleic acid,
tartaric acid,
citric acid,
succinic acid, and stearic acid;
aromatic carboxylic acids, such as benzoic acid,
p-t-butyl benzoate,
phthalic acid,
gallic acid,
salicylic acid, such as 3-isopropyl salicylate,
3-phenyl salicylate,
3-cyclohexyl salicylate, 3,5-di-t-butyl salicylate,
3-methyl-5-benzyl salicylate,
3-phenyl-5-(2,2-dimethylbenzyl)salicylate,
3,5-di-(2-methylbenzyl)salicylate and 2-hydroxyl-1-benzyl-3-naphtate;
salts derived from these aromatic carboxylic acids through displacement by such metals as zinc, magnesium, aluminum and titanium;
developers of phenolic resin, such as p-phenylphenol-formalin resin and p-butylphenol-acetylene resin, and
mixtures of these developers of phenolic resin and the metal salts of aromatic carboxylic acids described above.

Examples for the image stabilizer include
epoxycontaining diphenylsulfones, such as 4-benzyloxy-4'-(2-methylglycidyloxy)-diphenylsulfone,
and 4,4'-diglycidyloxydiphenylsulfone; and
1,4-diglycidyloxybenzene;
4-[α-(hydroxymethyl)benzyloxy]-4'-hydroxydiphenylsulfone;
2-propanol derivative;
salicylic acid derivative;
metal salts of oxynaphthoic acid derivatives (particulary, zinc salt);
metal salts of 2,2-methylenebis(4,6-t-butylphenyl)phosphate and other water-insoluble zinc-containing compounds.

Examples for the sensitizer include
higher fatty acid amides, such as the stearic amide;
benzamides;
anilide, such as stearic anilide, acetoacetic anilide and thioacetoanilide;
dibenzyl oxalate, di(4-methylbenzyl) oxalate, di(4-chlorobenzyl) oxalate, dimethyl phthalate,
dimethyl terephthalate, dibenzyl terephthalate, dibenzyl isophthalate,
and kinds of bis(t-butylphenol)s;
diphenylsulfone and its derivatives;
diethers of 4,4'-dihydroxydiphenylsulfone, such as 4,4'-dimethoxydiphenylsulfone,
4,4'-diethoxydiphenylsulfone,
4,4'-dipropoxydiphenylsulfone,
4,4'-diisopropoxydiphenylsulfone,
4,4'-dibutoxydiphenylsulfone,
4,4'-diisobutoxydiphenylsulfone,
4,4'-dipentyloxydiphenylsulfone and the 4,4'-dihexyloxydiphenylsulfone;
diethers of 2,4'-dihydroxydiphenylsulfone, such as 2,4'-dimethoxydiphenylsulfone,
2,4'-diethoxydiphenylsulfone,
2,4'-dipropoxydiphenylsulfone,
2,4'-diisopropoxydiphenylsulfone,
2,4'-dibutoxydiphenylsulfone,
2,4'-diisobutoxydiphenylsulfone,
2,4'-dipentyloxydiphenylsulfone and 2,4'-dihexyloxydiphenylsulfone; and
1,2-bis(phenoxy)ethane,
1,2-bis(4-methylphenoxy)ethane,
1,2-bis(3-methylphenoxy)ethane,
2-naphtholbenzyl ether,
diphenyl amine,
carbazole,
2,3-di-m-tolylbutane,
4-benzylbiphenyl,
4,4'-dimethylbiphenyl,
m-triphenyl,
di-β-naphthylphenylene diamine,
phenyl 1-hydroxynaphthoate,
2-naphthylbenzyl ether,
4-methylphenyl-biphenyl ether,
2,2-bis(3,4-dimethylphenyl)ethane,
2,3,5,6-tetramethyl-4'-methyldiphenylmethane and diphenyl carboxylate.

In particular, desirable sensitizers include;
Ethers, such as 1,2-bis(phenoxy)ethane,
1,2-bis(3-methylphenoxy)ethane and 2-naphthylbenzyl ether;
aromatic hydrocarbons, such as m-terphenyl,
4-benzylbiphenyl and di(4-methylbenzyl)oxalate;
diphenylsulfone and derivatives of diphenylsulfone;
diethers of 4,4'-dihydroxydiphenylsulfone; and
diethers of 2,4'-dihydroxydiphenylsulfone.

As the filler, silica, clay, kaolin, burned kaolin, talc, satin white, aluminum hydroxide, calcium carbonate, magnesium carbonate, zinc oxide, titanium oxide, barium sulfate, magnesium silicate, aluminum silicate, plastic pigment and the like may be used. In the recording material of the present invention, salts of alkaline earth metals are particularly preferable, and carbonates, such as calcium carbonate and magnesium carbonate are further preferable.

Examples for the dispersing agent include sulfosuccinic esters, such as dioctylsodium sulfosuccinate, sodium dodecylbenzene sulfonate,
and sodium salt and fatty acid salt of lauryl alcohol sulfuric ester.

Examples for the antioxidant include 2,2'-methylenebis(4-methyl-6-t-butylphenol),
2,2'-methylenebis(4-ethyl-6-t-butylphenol),
4,4'-propylmethylenebis(3-methyl-6-t-butylphenol),
4,4'-butylidenebis(3-methyl-6-t-butylphenol),
4,4'-thiobis(2-t-butyl-5-metylphenol),
1,1,3-tris(2-methyl-4-hydroxy-5-t-butylphenyl)butane,
1,1,3-tris(2-methyl-4-hydroxy-5-cyclohexylphenyl)butane and 4-{4-[1,1-bis(4-hydroxyphenyl)ethyl]-a,a-dimethylbenzyl}phenol.

As the desensitizer, aliphatic higher alcohols, polyethylene glycol, and guanidine derivatives and the like may be used.

Examples for the antitack agent include stearic acid, zinc stearate, calcium stearate, carnauba wax, paraffin wax and ester wax.

Examples for the photostabilizing agent include salicylic acid based ultraviolet radiation absorbents, such as phenyl salicylate,
p-t-butylphenyl salicylate and p-octylphenyl salicylate;
Benzophenone based ultraviolet radiation absorbents, such as the 2,4-dihydroxybenzophenone,
2-hydroxy-4-methoxybenzophenone,
2-hydroxy-4-benzyloxybenzophenone,
2-hydroxy-4-octyloxybenzophenone,
2-hydroxy-4-dodecyloxybenzophenone,
2,2'-dihydroxy-4-methoxybenzophenone,
2,2'-dihydroxy-4,4'-dimethoxybenzophenone,
2-hydroxy-4-metoxy-5-sulfobenzophenone and bis(2-methoxy-4-hydroxy-5-benzoilphenyl)methane; and
benzotriazole based ultraviolet radiation absorbents, such as 2-(2'-hydroxy-5'-methylphenyl)benzotriazole,
2-(2'-hydroxy-5'-t-buthylphenyl)benzotriazole,
2-(2'-hydroxy-3',5'-di-t-buthylphenyl)benzotriazole,
2-(2'-hydroxy-3'-t-buthyl-5'-methylphenyl)-5-chlorobenzotriazole,
2-(2'-hydroxy-3',5'-di-t-buthylphenyl)-5-chlorobenzotriazole,
2-(2'-hydroxy-3',5'-di-t-amylphenyl)benzotriazole,
2-[2'-hydroxy-3'-(3",4",5",6"-tetrahydrophthalimidemethyl)-5'-t-methylphenyl]benzotriazole,
2-(2'-hydroxy-5'-t-octylphenyl)benzotriazole, 2-[2'-hydroxy-3',5'-bis(α,α-dimethylbenzyl)phenyl]-2H-benzotriazole,
2-(2'-hydroxy-3'-dodecyl-5'-methylphenyl)benzotriazole,
2-(2'-hydroxy-3'-undecyl-5'-methylphenyl)benzotriazole,
2-(2'-hydroxy-3'-tridecyl-5'-methylphenyl)benzotriazole,
2-(2'-hydroxy-3'-tetradecyl-5'-methylphenyl)benzotriazole,
2-(2'-hydroxy-3'-pentadecyl-5'-methylphenyl)benzotriazole,
2-(2'-hydroxy-3'-hexadecyl-5'-methylphenyl)benzotriazole,
2-[2'-hydroxy-4'-(2"-ethylhexyl)oxyphenyl]benzotriazole,
2-[2'-hydroxy-4'-(2"-ethylhepthyl)oxy phenyl]benzotriazole,
2-[2'-hydroxy-4'-(2"-ethyloctyl)oxy phenyl]benzotriazole,
2-[2'-hydroxy-4'-(2"-propyloctyl)oxyphenyl]benzotriazole,
2-[2'-hydroxy-4'-(2"-propylheptyl)oxyphenyl]benzotriazole,
2-[2'-hydroxy-4'-(2"-propylhexyl)oxyphenyl]benzotriazole,
2-[2'-hydroxy-4'-(1"-ethylhexyl)oxyphenyl]benzotriazole,
2-[2'-hydroxy-4'-(1"-ethylheptyl)oxyphenyl]benzotriazole,
2-[2'-hydroxy-4'-(1'-ethyloctyl)oxyphenyl]benzotriazole,
2-[2'-hydroxy-4'-(1"-propyloctyl)oxyphenyl]benzotriazole,
2-[2'-hydroxy-4'-(1"-propylheptyl)oxyphenyl]benzotriazole,
2-[2'-hydroxy-4'-(1"-propylhexyl)oxyphenyl]benzotriazole,
2,2'-methylenebis[4-(1,1,3,3-tetramethylbutyl)-6-(2H-benzotriazole-2-yl)]phenol and a condensate of polyethylene glycol and methyl-3-[3-t-butyl-5-(2H-benzotriazole-2-yl)-4-hydroxyphenyl]propionate;

cyanoacrylate based ultraviolet radiation absorbents, such as 2'-ethylhexyl-2-cyano-3,3-diphenylacrylate and the ethyl-2-cyano-3,3-diphenylacrylate; and hindered amine based ultraviolet radiation absorbemts, such as bis(2,2,6,6-tetramethyl-4-piperidyl)sebacate, succinic acid-bis(2,2,6,6-tetramethyl-4-piperidyl) ester and 2-(3,5-di-t-butyl) malonate-bis(1,2,2,6,6-pentamethyl-4-piperidyl) ester; and 1,8-dihydroxy-2-acetyl-3-methyl-6-methoxy naphthalene.

Examples for the fluorescent dye include 4,4'-bis[2-anilino-4-(2-hydroxyethyl)amino-1,3,5-triazinyl-6-amino] stilbene-2,2'-disulfonic acid disodium salt,
4,4'-bis[2-anilino-4-bis(hydroxyethyl)amino-1,3,5-triazinyl-6-amino]stilbene-2,2'-disulfonic acid disodium salt,
4,4'-bis[2-methoxy-4-(2-hydroxyethyl)amino-1,3,5-triazinyl-6-amino]stilbene-2,2'-disulfonic acid disodium salt,
4,4'-bis[2-methoxy-4-(2-hydroxypropyl)amino-1,3,5-triazinyl-6-amino]stilbene-2,2'-disulfonic acid disodium salt,
4,4'-bis[2-m-sulfoanilino-4-bis(hydroxyethyl)amino-1,3,5-triazinyl-6-amino]stilbene-2,2'-disulfonic acid disodium salt,
4-[2-p-sulfoanilino-4-bis(hydroxyethyl)amino-1,3,5-triazinyl-6-amino]-4'-[2-m-sulfoanilino-4-bis(hydroxyethyl) amino-1,3,5-triazinyl-6-amino] stilbene-2,2'-disulfonic acid tetrasodium salt,
4,4'-bis[2-p-sulfoanilino-4-bis(hydroxyethyl)amino-1,3,5-triazinyl-6-amino]stilbene-2,2'-disulfonic acid tetrasodium salt,
4,4'-bis[2-(2,5-disulfoanilino)-4-phenoxyamino-1,3,5-triazinyl-6-amino]stilbene-2,2'-disulfonic acid hexasodium salt,
4,4'-bis[2-(2,5-disulfoanilino)-4-(p-methoxycarbonylphenoxy)amino-1,3,5-triazinyl-6-amino]stilbene-2,2'-disulfonic acid hexasodium salt,
4,4'-bis[2-(p-sulfophenoxy)-4-bis(hydroxyethyl)amino-1,3,5-triazinyl-6-amino]stilbene-2,2'-disulfonic acid tetrasodium salt,
4,4'-bis[2-(2,5-disulfoanilino)-4-formalinylamino-1,3,5-triazinyl-6-amino]stilbene-2,2'-disulfonic acid hexasodium salt and
4,4'-bis[2-(2,5-disulfoanilino)-4-bis(hydroxyethyl)amino-1,3,5-triazinyl-6-amino]stilbene-2,2'-disulfonic acid hexasodium salt.

Different kinds of material used for making each element of the color forming dye have been explained. The elements include the developer, the image stabilizer, the sensitizer, the filler, the dispersing agent, the antioxidant, the desensitizer, the antitack agent, the antifoamer, the photostabilizing agent and the fluorescent dye. In making each of the elements, every kind of material can be utilized alone without mixing with others. As an alternative, each kind of material can be utilized by mixing with any of the other kinds. The ratio of each element to be used with respect to a color forming dye is 0.1 to 15 parts by weight based on 1 part by weight of a color forming dye, and preferably 1 to 10 parts by weight.

The recording sheet provided by the present invention has a recording material layer created on a base sheet from a recording material provided by the present invention. The base sheet can be a paper base sheet, a synthetic resin film or a synthetic resin sheet. Examples for the paper base sheet include thin leaf paper, craft paper, titanium paper, linter paper, board paper, wood free paper, coated paper, art paper, vegetable paper, glassine paper, parchment paper, paraffine paper and recycled paper. Examples for the synthetic resin film or the synthetic resin sheet include the polyethylene, the polypropylene, the polyvinyl chloride, the polyvinylidene chloride, the ethylene-vinyl acetate copolymer, the ethylene-vinyl alcohol inter polymer, the polyethylene terephthalate, the polybutylene terephthalate, the polyethylene naphphthalate, the polymethyl methacrylate, the polymethyl acrylate, the polyethyl methacrylate, the polystyrene, the cellulose triacetate, the cellophane and the polycarbonate. In particular, use of paper base sheets is desirable. There are no particular limitations on the thickness of the base sheet. However, the thickness of the base sheet normally has a value in the range 1 to 500 micrometers Typically, the recording material layer is created by coating the base sheet with a solution or a dispersion of the recording material by adoption of a commonly known coating method. The amount of coating is dependent on the concentration of the solution or the dispersion liquid. However, it is 0.1 to 100 $g/m^2$, desirably 1 to 20 $g/m^2$ by dry weight.

Typical methods of coating the basic sheet with a solution or a dispersion of the recording material provided by the present invention include, but not limited to, a roll coat method, a curtain flow coat method, a Mayer bar coat method, a reversed coat method, a photogravure coat method, a photogravure reversed coat method, an air knife coat method, a kiss coat method, a blade coat method, a smooth coat method and a roll knife coat method.

In addition, the recording material layer may be created directly on the base sheet. As an alternative, the recording material layer may be created above the base sheet, with another layer such as an anchor coat layer sandwiched between the recording material layer and the base sheet. A protection layer may further be created on the recording material layer. The anchor coat layer and the protection layer may each be made from a solution or a dispersion, including one or several kinds of commonly known synthetic resin. If necessary, the solution or the dispersion may include the other aforementioned elements of the developer, the stabilizer, the sensitizer, the filler, the dispersing agent, the antioxidant, the desensitizer, the antitack agent, the antifoamer, the photo stabilizer and the fluorescent dye.

In particular, it is desirable to use thermal recording paper and pressure-sensitive copying paper as a material for making the recording sheet of the present invention. The thermal recording paper can be manufactured by preparing a dispersion, coating the upper surface of the base sheet with the dispersion and, then, drying the base sheet and the dispersion.

The dispersion is prepared by dissolving, for example, fine particles of the color forming dye and fine particles of the recording material into an aqueous solution of an aqueous binding agent, such as polyvinyl alcohol and the cellulose.

The pressure-sensitive copying paper can be manufactured by combining a color forming dye sheet and a developer sheet. The color formingdye sheet is made by coating the upper surface of a first paper base sheet with a color forming dye dispersion, which is prepared typically by dispersing microcapsules of a color forming dye by adoption of a commonly known method using a proper dispersion. On the other hand, the developer sheet is made by coating the upper surface of a second paper base sheet with the dispersion of a developer. During these processes, the recording material provided by the present invention is dispersed into the color forming dye dispersion or the dispersion of the developer, or both the dispersions.

The pressure-sensitive copying paper can also be manufactured as a unit comprising an upper sheet of paper and a lower sheet of paper. The lower surface of the upper sheet of paper is coated with microcapsules, each including the organic solvent solution of the color forming dye and being retained on the surface. The microcapsules also serve as a support material. The upper surface of the lower sheet of paper is coated with the developer(an acidic substances), which also is retained on the surface. As another alternative, the pressure-sensitive copying paper is manufactured as a piece of self content paper. One face of the self content paper is coated with both the developer and microcapsules each including the organic solvent solution of the color forming dye. As the developer for the pressure-sensitive copying paper, developers including, but not limited to, any of the aforementionated typical developers for the pressure-sensitive paper can be used.

BEST MODES FOR CARRYING OUT THE INVENTION

Preferred embodiments of the present invention are described in detail as follows. However, the scope of the present invention is not limited to these embodiments. It is to be noted that, unless otherwise specified, the technical term 'unit' used in the following description means a 'weight unit'. A image density (Macbeth value) and a background density (Macbeth value) have been measured by using a Macbeth reflection densitometer manufactured by Macbeth Corporation with a model number of RD-514 and filter number #106.

SYNTHESIS EXAMPLE 1

Synthesis of N-(4'-hydroxyphenylthio)acetyl-2-hydroxyaniline 109.1 g (1 mol) of 2-aminophenol, 84.1 g (1 mol) of sodium bicarbonate, 900 mL of acetonitrile and 100 mL of water were added under room temperature into a 2 L flask with four inlets and attached with a stirrer and a thermometer. The internal temperature was cool down to 10° C. and 112.9 g (1 mol) of chloroacetyl chloride was added to the solution over a period of 3 hours and stirred for 3 hours at room temperature. Following to the completion of the reaction, 10 mL of methanol was added, and then acetonitrile was distilled out under reduced pressure and the resultant residue was subjected to recrystallization with toluene. Then, salt was taken out in a cleaning process using water to obtain 2-chloroacetyl-2-hydroxyaniline.

Then, 126.2 g (1 mol) of 4-mercaptophenol, 66 g (1 mol) of potassium hydroxide and 1 L of methanol were added under room temperature into a 3 L flask with four inlets and attached with a stirrer and a thermometer. After confirming that potassium hydroxide added is completely dissolved, temperature inside the resultant solution was cool down to 10° C., then 2-chloroacetyl-2-hydroxyaniline obtained as a result of the reaction described above was added to the solution and stirred at room temperature for 3 hours. Following to the completion of the reaction, 2 L of water was added and separated crystals was filtered to give 210 g of N-(4'-hydoxyphenylthio)acetyl-2-hydroxyaniline. The yield was 76% and the melting point was in a range of 176 to 179° C.

SYNTHESIS EXAMPLE 2

Synthesis of N-(4'-hydroxyphenylthio)acetyl-4-hydroxyaniline

Synthesis example 2 was obtained according to the same process as described in the synthesis example 1, except that, 2-aminophenol is replaced by 4-aminophenol. The melting point was in a range 163 to 164° C.

SYNTHESIS EXAMPLE 3

Synthesis of N-(4'-hydroxyphenylthio)acetyl-3-hydroxyaniline

Synthesis example 3 was obtained according to the same process as described in the synthesis example 1, except that, 2-aminophenol is replaced by 3-aminophenol. The melting point was in a range 171 to 173° C.

In addition to synthesis examples 1 to 3 described above, as a method of mixing compositions provided by the present invention, it is possible to adopt other methods such as a method of making reactions using the hydroxy aniline compounds each as a raw material as is the case with the following synthesis examples.

SYNTHESIS EXAMPLE 4

Synthesis of N-(4'-hydroxyphenylthio)acetyl-2-hydroxyaniline and N-(4'-hydroxyphenylthio)acetyl-4-hydroxyaniline (Mixing Ratio of 1:1)

54.6 g (0.5 mol) of 2-aminophenol, 54.6 g (0.5 mol) of 4-aminophenol, 84.1 g (1 mol) of sodium bicarbonate, 900 mL of acetonitrile and 100 mL of water were added under room temperature into a 2 L flask with four inlets and attached with a stirrer and a thermometer. The internal temperature was cool down to 10° C. and 112.9 g (1 mol) of chloroacetyl chloride was added to the solution over a period of 3 hours and stirred for 3 hours at room temperature. Following to the completion of the reaction, 10 mL of methanol was added, and then acetonitrile was distilled out under reduced pressure and the resultant residue was subjected to recrystallization with toluene. Then, salt was taken out in a cleaning process using water to obtain a mixture of 2-chloroacetyl-2-hydroxyaniline and 2-chloroacetyl-4-hydroxyaniline.

Then, 126.2 g (1 mol) of 4-mercaptophenol, 66 g (1 mol) of potassium hydroxide and 1 L of methanol were added under room temperature into a 3 L flask with four inlets and attached with a stirrer and a thermometer. After confirming that potassium hydroxide added is completely dissolved, temperature inside the resultant solution was cool down to 10° C., then a mixture of 2-chloroacetyl-2-hydroxyaniline and 2-chloroacetyl-4-hydroxyaniline obtained as a result of the reaction described above was added to the solution and stirred at room temperature for 3 hours. Following to the completion of the reaction, 2 L of water was added and separated crystals were filtered to give 231 g of a mixture of N-(4'-hydoxyphenylthio)acetyl-2-hydroxyaniline and N-(4'-hydoxyphenylthio)acetyl-4-hydroxyaniline (a mixing ratio of about 50%:50%). The yield was 80% and the melting point was in a range of 147 to 153° C.

First Embodiment (Preparation of the Thermal Recording Paper)

First of all, dispersion (liquids A to D) including components described below were prepared. It is to be noted that the components have each been well ground by using a sand grinder.

Dye Dispersion (Liquid A)

The dye dispersion referred to as liquid A is a liquid obtained as a result of dispersing 3-di-n-butylamino-6-methyl-7-anilinofluoran with a weight of 16 units in 84 units of an aqueous solution containing 10% polyvinyl alcohol.

Developer Dispersion (Liquid B)

The developer dispersion referred to as liquid B is a liquid obtained as a result of dispersing N-(4'-hydroxyphenylthio)acetyl-2-hydroxyaniline with a weight of 8 units and N-(4'-hydroxyphenylthio)acetyl-4-hydroxyaniline with a weight of 8 units in 84units of an aqueous solution containing 10% polyvinyl alcohol.

Sensitizer Dispersion (Liquid C)

The sensitizer dispersion referred to as liquid C is a liquid obtained as a result of dispersing di(4-methylbenzyl) oxalate with a weight of 16 in 84 units of an aqueous solution containing 10% polyvinyl alcohol.

Filler Dispersion (Liquid D)

The filler dispersion liquid referred to as liquid D is a liquid obtained as a result of dispersing calcium carbonate with a weight of 27.8 units in 26.2 units of an aqueous solution containing 10% polyvinyl alcohol and water with a weight of 71 units.

These dispersions were mixed at weight proportions of liquid A:liquid B:liquid C:liquid D set at 1:2:1:4 in order to prepare a coating liquid of a recording material for the thermal recording paper.

Then, the surface of a piece of base paper was coated with 5.5 $g/m^2$ (dry weight) of the coating liquid of the recording material by using a wire rod manufactured by Wave Star Corporation with a commodity name of Wire Bar and a commodity number of 12. After a drying process, a calendaring process was carried out to make the thermal recording paper. Visual observation of the produced thermal recording paper confirmed that there is no background fogging.

Second Embodiment

In accordance with a second embodiment, a recording material was prepared in order to manufacture the thermal recording paper by adoption of the same method as the first embodiment except that liquid E described below was used as a substitute for the developer dispersion referred to as liquid B.

Developer Dispersion (Liquid E)

A developer dispersion referred to as liquid E is a liquid obtained as a result of dispersing N-(4'-hydroxyphenylthio)acetyl-2-hydroxyaniline with a weight of 8 units and N-(4'-hydroxyphenylthio)acetyl-3-hydroxyaniline with a weight of 8 units in 84 units of an aqueous solution containing 10% polyvinyl alcohol.

Visual observation of the produced thermal recording paper confirmed that there is no background fogging.

Third Embodiment

In accordance with a third embodiment, a recording material was prepared in order to manufacture the thermal recording paper by adoption of the same method as the first embodiment except that liquid F described below was used as a substitute for the developer dispersion liquid referred to as liquid B.

Developer Dispersion (Liquid F)

A developer dispersion referred to as liquid F is a liquid obtained as a result of dispersing N-(4'-hydroxyphenylthio)acetyl-2-hydroxyaniline with a weight of 5.3 units, N-(4'-hydroxyphenylthio)acetyl-3-hydroxyaniline with a weight of 5.3 units and N-(4'-hydroxyphenylthio)acetyl-4-hydroxyaniline with a weight of 5.3 units in 84 units of an aqueous solution containing 10% polyvinyl alcohol.

Visual observation of the produced thermal recording paper confirmed that there is no background fogging.

Comparison Example 1

In accordance with comparison example 1, a recording material was prepared in order to manufacture the thermal recording paper by adoption of the same method as the first embodiment except that liquid K described below was used as a substitute for the developer dispersion referred to as liquid B.

Developer Dispersion (Liquid K)

A developer dispersion referred to as liquid K is a liquid obtained as a result of dispersing 2,4'-dihydroxydiphenylsulfone with a weight of 16 units in 84 units of an aqueous solution containing 10% polyvinyl alcohol.

Comparison Example 2

In accordance with comparison example 2, a recording material was prepared in order to manufacture the thermal recording paper by adoption of the same method as the first embodiment except that liquid L described below was used as a substitute for the developer dispersion referred to as liquid B.

Developer Dispersion (Liquid L)

A developer dispersion referred to as liquid L is a liquid obtained as a result of dispersing N-(4'-hydroxyphenylthio)acetyl-2-hydroxyaniline with a weight of 16 units in 84 units of an aqueous solution containing 10% polyvinyl alcohol.

EXPERIMENT EXAMPLE 1

Measurement of Dynamic Sensitivities

A portion of every piece of thermal recording paper made in accordance with each of the first to third embodiments as well as each of comparison examples 1 and 2 was cut out and used as an experiment paper specimen. For each experiment paper specimen, a coloring instrument for dynamic sensitivity was used. The apparatus was manufactured by Ohkura Electric Corporation (model number TH-PMD). Subsequently, heat energy was added under conditions of 0.38 and 0.50 m J per dot. Then, image density (Macbeth values) of the experiment paper specimens were measured to give results of measurement as shown in the first table. As is obvious from the first table, the pieces of thermal recording paper, which were made in accordance with the first to third embodiments, are known to each have a high dynamic sensitivity of the same order as the pieces of thermal recording paper, which were made in accordance with comparison examples 1 and 2.

EXPERIMENT EXAMPLE 2

Heat & Humidity Resistance Tests of Image

A portion of every piece of thermal recording paper made in accordance with each of the first to third embodiments as well as each of comparison examples 1 and 2 was cut out and used as an experiment paper specimen. Subsequently, heat energy was added to get the state of saturated density of image in the same way as Experiment Example 1. Each of the experiment paper specimens in the state of saturated colored was then kept for 24 hours at a temperature of 50° C. and a humidity of 80% in a incubator controlled humidity and temperature manufactured by Futaba Science Corporation (model number GL-42). Right after the state of saturated colored and keeping after 24-hour in the incubator controlled humidity and temperature, image density (Macbeth values) of the experiment paper specimens were measured to give results of measurement as shown in the first table. As is obvious from the first table, the pieces of thermal recording paper, which were made in accordance with the first to third embodiments, are known to each have heat and humidity resistance superior to the pieces of thermal recording paper, which were made in accordance with comparison examples 1 and 2.

EXPERIMENT EXAMPLE 3

Heat Resistance Tests of Image

A portion of every piece of thermally sensitive recording paper made in accordance with each of the first to third embodiments as well as each of comparison examples 1 and 2 was cut out and used as an experiment paper specimen. Subsequently, heat energy was added to get the state of saturated density of image in the same way as experiment example 1. Each of the experiment paper specimens in the state of saturated colored was then kept for 24 hours at a temperature of 90° C. in a constant temperature oven manufactured by Yamato Science Corporation (model number DK-400). Right after the state of saturated colored and keeping after the 24-hour in the constant temperature oven, image density (Macbeth values) of the experiment paper specimens were measured to give results of measurement as shown in the first table. As is obvious from the first table, the pieces of thermal recording paper, which were made in accordance with the first to third embodiments, are known to each have a heat resistance superior to the pieces of thermal recording paper, which were made in accordance with comparison examples 1 and 2.

EXPERIMENT EXAMPLE 4

Light Resistance Tests of Image

A portion of every piece of thermal recording paper made in accordance with each of the first to third embodiments as well as each of comparison examples 1 and 2 was cut out and used as an experiment paper specimen. Subsequently, heat energy was added to get the state of saturated density of image in the same way as experiment example 1. Then, after an ultraviolet ray beam having a wavelength of 380 nm was radiated to each of the experiment paper specimens for 24 hours or 72 hours by using a UV auto-fade-mater equipped with an Ultraviolet Carbon Arc lamp manufactured by Suga Testing Equipment Corporation with a commodity name of ultraviolet long-life fade meter and a model number of FAL-5, image density (Macbeth values) of the experiment paper specimens were measured to give measurement results and remaining rates(residual) summarized as shown in the first table. A remaining rate (residual) expressed in terms of percents is defined as a ratio of the post-experiment image density to a pre-experiment image density. As is obvious from the first table, the pieces of thermal recording paper, which were made in accordance with the first to third embodiments, are known to each have a light resistance of the same order as the pieces of thermal recording paper, which were made in accordance with comparison examples 1 and 2.

EXPERIMENT EXAMPLE 5

Plasticizer Resistance Tests of Image Part-I

A portion of every piece of thermal recording paper made in accordance with each of the first to third embodiments as well as each of comparison examples 1 and 2 was cut out and used as an experiment paper specimen. Subsequently, heat energy was added to get the state of saturated density of image in the same way as Experiment Example 1. Then, a vinyl-chloride wrap film including a plasticizer was stuck on to the color-developing surface of each of the experiment paper specimens. The experiment paper specimens were then kept in this state for eight hours at a temperature of 25° C.

Right after the state of saturated color development and after the eight-hour storage period at the temperature of 25° C., image density (Macbeth values) of the experiment paper specimens were measured to give results of measurement as shown in the first table. As is obvious from the first table, the pieces of thermal recording paper, which were made in accordance with the first to third embodiments, are known to each have a plasticizer resistance superior to the pieces of thermal recording paper, which were made in accordance with comparison examples 1 and 2.

EXPERIMENT EXAMPLE 6

Water Resistance Tests of Image Part-I

A portion of every piece of thermal recording paper made in accordance with each of the first to third embodiments as well as each of comparison examples 1 and 2 was cut out and used as an experiment paper specimen. Subsequently, heat energy was added to get the state of saturated density of image in the same way as experiment example 1. Then, each of the experiment paper specimens was submerged in pure water at a temperature of 25° C. for seven days. Right after the state of saturated colored and after the seven-day submersion period at a temperature of 25° C., image density (Macbeth values) of the experiment paper specimens were measured to give results of measurement as shown in the first table. As is obvious from the first table, the pieces of thermal recording paper, which were made in accordance with the first to third embodiments, are known to each have a water resistance superior to the pieces of thermal recording paper, which were made in accordance with comparison examples 1 and 2.

The results of experiment examples 1 to 6 prove that the thermal recording paper provided by the present invention has an excellent dynamic sensitivity as well as a heat and humidity resistance, a heat resistance, a light resistance, a plasticizer resistance and a water resistance, which are all also excellent as well.

Then, as references, experiments were carried out on pieces of thermal recording paper using a substitute for the sensitizer or dye of the thermal recording paper made in accordance with the first embodiment of the present invention.

Fourth Embodiment

In accordance with a fourth embodiment, a recording material was prepared in order to manufacture the thermal recording paper by adoption of the same method as the first embodiment except that liquid G described below was used as a substitute for the sensitizer dispersion referred to as liquid C.

Sensitizer Dispersion (liquid G)

A sensitizer dispersion referred to as liquid G is a liquid obtained as a result of dispersing 1,2-bis(phenoxy)ethane with a weight of 16 units in 84 units of an aqueous solution containing 10% polyvinyl alcohol.

Visual observation of the produced thermal recording paper confirmed that there is no background fogging.

Fifth Embodiment

In accordance with a fifth embodiment, a recording material was prepared in order to manufacture the thermal recording paper by adoption of the same method as the first embodiment except that liquid H described below was used as a substitute for the sensitizer dispersion referred to as liquid C.

Sensitizer Dispersion (Liquid H)

A sensitizer dispersion liquid referred to as liquid H is a liquid obtained as a result of dispersing diphenylsulfone with a weight of 16 units in 84 units of an aqueous solution containing 10% polyvinyl alcohol.

Visual observation of the produced thermal recording paper confirmed that there is no background fogging.

Sixth Embodiment

In accordance with a sixth embodiment, a recording material was prepared in order to manufacture the thermal recording paper by adoption of the same method as the first embodiment except that liquid I described below was used as a substitute for the dye dispersion dispersion to as liquid A.

Dye Dispersion (Liquid I)

A dye dispersion referred to as liquid I is a liquid obtained as a result of dispersing 3-(N-methyl-N-propylamino)-6-methyl-7-anilinofluoran with a weight of 16 units in 84 units of an aqueous solution containing 10% polyvinyl alcohol.

Visual observation of the produced thermal recording paper confirmed that there is no background fogging.

Seventh Embodiment

In accordance with a seventh embodiment, a recording material was prepared in order to manufacture the thermal recording paper by adoption of the same method as the first embodiment except that liquid J described below was used as a substitute for the dye dispersion dispersion to as liquid A.

Dye Dispersion (Liquid J)

A dye dispersion referred to as liquid J is a liquid obtained as a result of dispersing 3-(N-cyclohexyl-N-methylamino)-6-methyl-7-anilinofluoran with a weight of 16 units in 84 units of an aqueous solution containing 10% polyvinyl alcohol.

Visual observation of the produced thermal recording paper confirmed that there is no background fogging.

EXPERIMENT EXAMPLE 7

Heat Resistance Tests of Background

A portion of every piece of thermal recording paper made in accordance with each of the first, fourth and fifth embodiments was cut out and used as an experiment paper specimen. Subsequently, each of the experiment paper specimens was put in a Constant Temperature oven at temperatures of 90° C. and 100° C. for 24 hours. The Constant Temperature oven was manufactured by Yamato Corporation (model number DK-400).

After each of the experiment paper specimens was put in a Constant Temperature oven for 24 hours, background density (Macbeth values) of the experiment paper specimens were measured to give results of measurement as shown in the second table. As is obvious from the second table, by selecting a proper sensitizer, it is known that the heat resistance of background, which are about equal to each other at the temperature of 90° C., can be further improved at the temperature of 100° C.

TABLE 2

(Results of heat resistance tests of background)

| | Background density after heat resistance tests | |
|---|---|---|
| | Macbeth value (90° C.) | Macbeth value (100° C.) |
| First embodiment | 0.11 | 0.26 |
| Fourth embodiment | 0.10 | 0.15 |
| Fifth embodiment | 0.11 | 0.17 |

EXPERIMENT EXAMPLE 8

Plasticizer Resistance Tests of Image Part-II

A portion of every piece of thermal recording paper made in accordance with each of the first, sixth and seventh embodiments was cut out and used as an experiment paper specimen. Subsequently, heat energy was added to get the state of saturated density of image in the same way as experiment example 1. Then, a vinyl-chloride wrap film including a plasticizer was stuck to the color-developing surface of each of the experiment paper specimens. The experiment paper specimens were then kept in this state for eight hours at a temperature of 25° C.

Right after the state of saturated colored and keeping after the eight-hour at 25° C., image density (Macbeth values) of the experiment paper specimens were measured to give results of measurement as shown in the third table. As is obvious from the third table, by selecting a proper dye, it is known that plasticizer resistance of image can be further improved.

EXPERIMENT EXAMPLE 9

Water Resistance Tests of Image Part-II

A portion of every piece of thermal recording paper made in accordance with each of the first, sixth and seventh embodiments and used as an experiment paper specimen. Subsequently, heat energy was added to get the state of saturated density of image in the same way as experiment example 1. Then, each of the experiment paper specimens was submerged in pure water at a temperature of 25° C. for seven days. Right after the state of saturated colored and after the seven-day submersion period at the temperature of 25° C., image density (Macbeth values) of the experiment paper specimens were measured to give results of measurement as shown in the third table. As is obvious from the third table, by selecting a proper dye, it is known that the water resistance of image can be further improved.

TABLE 3

(Results of plasticizer resistance tests-part II and water resistance tests-part II)

| | Original | Image density after plasticizer resistance test | | Image density after water resistance test | |
|---|---|---|---|---|---|
| | Macbeth value | Macbeth value | Residual (%) | Macbeth value | Residual (%) |
| First embodiment | 1.17 | 0.39 | 33 | 0.85 | 73 |
| Reference example 3 | 1.18 | 0.65 | 55 | 1.09 | 92 |
| Reference example 4 | 1.20 | 0.74 | 62 | 0.94 | 78 |

Residual expressed in terms of percents is defined as a ratio of the post-experiment image density to a pre-experiment image density.

Eighth Embodiment

Manufacture of Thermal Recording Paper

Firstly, dispersion liquids (liquids A''' to E''') containing the components below were prepared. It is to be noted that each component used has been well ground by using a sand grinder.

| | |
|---|---|
| Dye dispersion liquid (liquid A''') | |
| 3-di-n-butylamino-6-methyl-7-anilinofluoran | 16 parts |
| 10% polyvinyl alcohol aqueous solution | 84 parts |
| Developer dispersion liquid (liquid B''') | |
| a mixture of 8 parts of N-(4'-hydroxyphenylthio)acetyl-2-hydroxyaniline and 8 parts of N-(4'-hydroxyphenylthio)acetyl-4-hydroxyaniline | 84 parts |
| 10% polyvinyl alcohol aqueous solution | |
| Sensitizer dispersion liquid (liquid C''') | |
| di(4-methylbenzyl) oxalate | 16 parts |
| 10% polyvinyl alcohol aqueous solution | 84 parts |
| Image stabilizer dispersion liquid (liquid D''') | |
| a mixture of 4-4'-[oxybis(ethylene-p-phenylenesulfonyl)]diphenol (greater than or equal to 40% is included) and the compound represented by the following Formula: 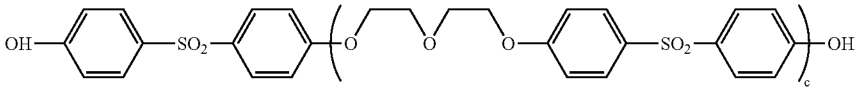 (In the Formula, c represents an integer of 2 to 10.) | 16 parts |
| 10% polyvinyl alcohol aqueous solution | 84 parts |
| Filler dispersion liquid (liquid E''') | |
| calcium carbonate | 27.8 parts |
| 10% polyvinyl alcohol aqueous solution | 26.2 parts |
| water | 71 parts |

The coating liquid of the recording material for the thermal recording paper was prepared by mixing these dispersions liquids in a proportion of 1 part per weight of liquid A''', 1.5 parts per weight of liquid B''', 1 part per weight of liquid C''', 0.5 parts per weight of liquid D''', and 4 parts per weight of liquid E'''.

Next, the coating liquid of the recording material was coated (coating weight: dry weight of about 5.5 $g/m^2$) to a white colored paper by using a wire rod (trade name: Wire Bar, No. 12, manufactured by Wave Star Corporation). After drying, a calendaring process was performed and the thermal recording paper was manufactured. Visual observation of the produced thermal recording paper confirmed that there was no background fogging.

Ninth Embodiment

Manufacture of Thermal Recording Paper

The thermal recording paper was manufactured by preparing the recording material by the same method as in Eighth embodiment except that di(4-methylbenzyl)oxalate in the sensitizer dispersion liquid (liquid C''') was substituted for dimethyl terephthalate. Visual observation of the produced thermal recording paper confirmed that there was no background fogging.

Comparison Example 3

A thermal recording paper was manufactured by preparing the recording material by the same method as in Eighth embodiment except that the image stability dispersion liquid (liquid D''') of Eighth embodiment was not used and the composition of liquid C''' in the coating liquid was 1 part per weight.

EXPERIMENT EXAMPLE 10

Plasticizer Resistance Tests of Image Part-III

A portion of the thermal recording papers manufactured in Eighth and Ninth embodiments, and Comparison Example 3 was cut out and these cutout pieces each was used as a test paper. For each test paper, a thermal paper color-developing test apparatus (trade name: TH-PMD, manufactured by Okura Electric Corporation) was used. Heat was added under conditions of 0.08 to 0.72 mJ per dot and each test paper was saturated color-developed in a checkered pattern. Next, a polyvinyl chloride wrap film was stuck to the color developed surface and the reverse surface of each test paper. The test papers were then kept in this state for 24 hours at 40° C. The optical density of the images was measured by a Macbeth densitometer (trade name: RD-514, filter used: #106, manufactured by Macbeth Corporation) directly after being saturated color developed and after being kept for 24 hours at 40° C. The results are shown in Table 4.

TABLE 4

(Test Results of the Image's Plasticizer Resistance)

| | Color-Developed Image (Before Test) | Color-Developed Image (After Test) | Image Residual Ratio (%) |
|---|---|---|---|
| Eighth embodiment | 1.35 | 0.76 | 56 |
| Ninth embodiment | 1.29 | 0.91 | 70 |
| Comparison Example 3 | 1.36 | 0.44 | 33 |

salad oil and kept for 24 hours at room temperature. The optical density of the images was measured by a Macbeth densitometer directly after being saturated color developed and after being kept for 24 hours at room temperature. The results are shown in Table 5.

TABLE 5

(Test Results of the Image's Oil Resistance)

| | Color-Developed Image (Before Test) | Color-Developed Image (After Test) | Image Residual Ratio (%) |
|---|---|---|---|
| Eighth embodiment | 1.35 | 0.77 | 57 |
| Ninth embodiment | 1.29 | 0.82 | 64 |
| Comparison Example 3 | 1.36 | 0.18 | 13 |

INDUSTRIAL APPLICABILITY

As described above, in accordance with the present invention, it is possible to provide a recording material and a recording sheet that cause no background fogging phenomenon and have an excellent dynamic sensitivity as well as an excellent image stability, particularly, such as a heat and humidity resistance, a heat resistance, a light resistance, a plasticizer resistance and a water resistance. In addition, it is possible to provide a recording material and a recording sheet wherein, if necessary, by selecting a sensitizer in applications of the recording material and the recording sheet, their heat resistance of background can be improved and, by selecting a proper dye in applications of the recording material and the recording sheet, their plasticizer resistance of image as well as their water resistance of image can be improved.

| | Dynamic sensitivity and Image stability | | | | | | | | | | | | |
|---|---|---|---|---|---|---|---|---|---|---|---|---|---|
| | Dynamic sensitivity | | Heat and Humidity resistance | | Heat resistance | | Light resistance | | | Plasticizer resistance | | Water resistance | |
| | 0.38 mJ/dot | 0.5 mJ/dot | original | After test <residual %> | Original | After test <Residual %> | Original | After test for 24 hours <Residual %> | After test for 72 hours <Residual %> | Original | After test <Residual %> | Original | After test <Residual %> |
| First embodiment | 0.45 | 0.96 | 1.14 | 1.24 <109> | 1.14 | 1.27 <111> | 1.14 | 1.00 <88> | 0.84 <74> | 1.12 | 0.66 <59> | 1.12 | 0.93 <83> |
| Second embodiment | 0.51 | 1.06 | 1.19 | 1.23 <104> | 1.19 | 1.26 <106> | 1.19 | 1.04 <87> | 0.84 <71> | 1.14 | 0.50 <44> | 1.14 | 0.97 <85> |
| Third embodiment | 0.45 | 0.94 | 1.09 | 1.24 <114> | 1.09 | 1.24 <114> | 1.09 | 0.90 <83> | 0.72 <66> | 1.10 | 0.63 <58> | 1.10 | 0.90 <82> |
| Comparison example 1 | 0.78 | 1.23 | 1.27 | 1.17 <92> | 1.27 | 1.05 <83> | 1.27 | 1.00 <79> | 0.82 <64> | 1.23 | 0.50 <41> | 1.23 | 0.96 <78> |
| Comparison example 2 | 0.48 | 1.07 | 1.23 | 0.51 <42> | 1.23 | 0.36 <30> | 1.23 | 1.11 <91> | 0.99 <80> | 1.22 | 0.15 <13> | 1.22 | 0.79 <65> |

EXPERIMENT EXAMPLE 11

Oil Resistance Test of Image

By the same method as in Experiment example 10, each of the saturated color-developed test papers were immersed in

What is claimed is:

1. A composition comprising:

at least one type of a compound represented by Formula (1); wherein (1)

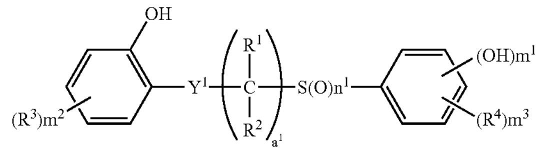

$R^1$ and $R^2$ each independently represent hydrogen or $C_1$-$C_6$ alkyl, $a^1$ represents an integer of 1 to 6, $n^1$ represents 0, 1 or 2, $m^1$ represents 0 or an integer in the range of 1 to 3, $R^3$ and $R^4$ each independently represent nitro, carboxyl, halogen, $C_1$-$C_6$ alkyl or $C_2$-$C_6$ alkenyl, $m^2$ and $m^3$ each independently represent 0, 1 or 2;

$R^3$ and $R^4$ may be different to each other when $m^2$ and $m^3$ each represent 2, $Y^1$ represents CO or $NR^5CO$ wherein $R^5$ represents hydrogen or $C_1$-$C_6$ alkyl); and at least one of the group consisting of a compound represented by Formula (2);

wherein (2)

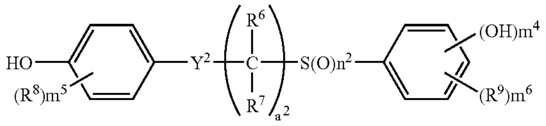

$R^6$ and $R^7$ each independently represent hydrogen or $C_1$-$C_6$ alkyl, $a^2$ represents an integer of 1 to 6, $n^2$ represents 0, 1 or 2, $m^4$ represents 0 or an integer in the range of 1 to 3, $R^8$ and $R^9$ each independently represent nitro, carboxyl, halogen, $C_1$-$C_6$ alkyl or $C_2$-$C_6$ alkenyl, $m^5$ and $m^6$ each independently represent 0, 1 or 2;

$R^8$ and $R^9$ may be different to each other when $m^5$ and $m^6$ each represent 2, $Y^2$ represents CO or $NR^{10}CO$ wherein $R^{10}$ represents hydrogen or $C_1$-$C_6$ alkyl; and a compound represented by Formula (3); wherein (3)

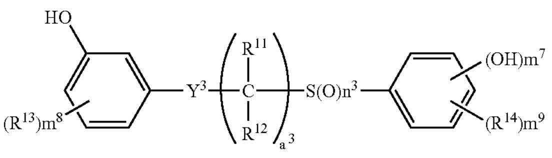

$R^{11}$ and $R^{12}$ each independently represent hydrogen or $C_1$-$C_6$ alkyl, $a^3$ represents an integer of 1 to 6, $n^3$ represents 0, 1 or 2, $m^7$ represents 0 or an integer in the range of 1 to 3, $R^{13}$ and $R^{14}$ each independently represent nitro, carboxyl, halogen, $C_1$-$C_6$ alkyl or $C_2$-$C_6$ alkenyl, $m^8$ and $m^9$ each independently represent 0, 1 or 2;

$R^{13}$ and $R^{14}$ may be different to each other when $m^8$ and $m^9$ each represent 2, $Y^3$ represents CO or $NR^{15}CO$ wherein $R^{15}$ represents hydrogen or $C_1$-$C_6$ alkyl.

2. A recording material comprising:

a compound represented by Formula (1); wherein (1)

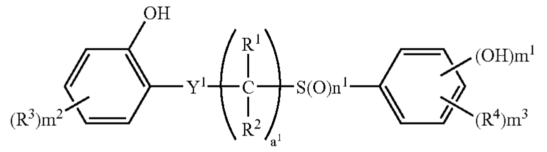

$R^1$ and $R^2$ each independently represent hydrogen or $C_1$-$C_6$ alkyl, $a^1$ represents an integer of 1 to 6, $n^1$ represents 0, 1 or 2, $m^1$ represents 0 or an integer in the range of 1 to 3, $R^3$ and $R^4$ each independently represent nitro, carboxyl, halogen, $C_1$-$C_6$ alkyl or $C_2$-$C_6$ alkenyl, $m^2$ and $m^3$ each independently represent 0, 1 or 2;

$R^3$ and $R^4$ may be different to each other when $m^2$ and $m^3$ each represent 2, $Y^1$ represents CO or $NR^5CO$ wherein $R^5$ represents hydrogen or $C_1$-$C_6$ alkyl; and at least one of the group consisting of a compound represented by Formula (2);

wherein (2)

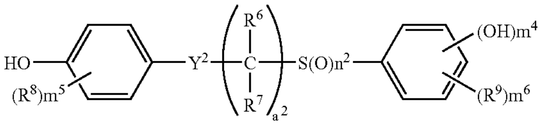

$R^6$ and $R^7$ each independently represent hydrogen or $C_1$-$C_6$ alkyl, $a^2$ represents an integer of 1 to 6, $n^2$ represents 0, 1 or 2, $m^4$ represents 0 or an integer in the range of 1 to 3, $R^8$ and $R^9$ each independently represent nitro, carboxyl, halogen, $C_1$-$C_6$ alkyl or $C_2$-$C_6$ alkenyl, $m^5$ and $m^6$ each independently represent 0, 1 or 2;

$R^8$ and $R^9$ may be different to each other when $m^5$ and $m^6$ each represent 2, $Y^2$ represents CO or $NR^{10}CO$ wherein $R^{10}$ represents hydrogen or $C_1$-$C_6$ alkyl; and a compound represented by Formula (3); wherein (3)

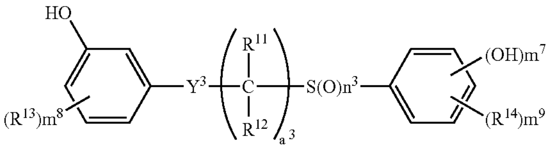

$R^{11}$ and $R^{12}$ each independently represent hydrogen or $C_1$-$C_6$ alkyl, $a^3$ represents an integer of 1 to 6, $n^3$ represents 0, 1 or 2, $m^7$ represents 0 or an integer in the range of 1 to 3, $R^{13}$ and $R^{14}$ each independently represent nitro, carboxyl, halogen, $C_1$-$C_6$ alkyl or $C_2$-$C_6$ alkenyl, $m^8$ and $m^9$ each independently represent 0, 1 or 2;

$R^{13}$ and $R^{14}$ may be different to each other when $m^8$ and $m^9$ each represent 2, $Y^3$ represents CO or $NR^{15}CO$ wherein $R^5$ represents hydrogen or $C_1$-$C_6$ alkyl.

3. A recording material according to claim 2, wherein a total content quantity of the compound represented by Formula (2) in claim 2 and the compound represented by Formula (3) in claim 2 is in the range of 5 to 500 parts by weight relative to 100 parts by weight of the compound represented by Formula (1) in claim 2.

4. A recording sheet comprising a base sheet and a recording material layer made from a recording material on the said base sheet, the recording material comprising:

at least one type of a compound represented by Formula (1); wherein (1)

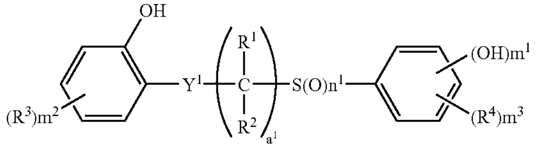

$R^1$ and $R^2$ each independently represent hydrogen or $C_1$-$C_6$ alkyl, $a^1$ represents an integer of 1 to 6, $n^1$ represents 0, 1 or 2, $m^1$ represents 0 or an integer in the range of 1 to 3, $R^3$ and $R^4$ each independently represent nitro, carboxyl, halogen, $C_1$-$C_6$ alkyl or $C_2$-$C_6$ alkenyl, $m^2$ and $m^3$ each independently represent 0, 1 or 2, $R^3$ and $R^4$ may be different to each other when $m^2$ and $m^3$ each represent 2, $Y^1$ represents CO or $NR^5CO$ wherein $R^5$ represents hydrogen or $C_1$-$C_6$ alkyl); and at least one of the group consisting of a compound represented by Formula (2);

$R^6$ and $R^7$ each independently represent hydrogen or $C_1$-$C_6$ alkyl, $a^2$ represents an integer of 1 to 6, $n^2$ represents 0, 1 or 2, $m^4$ represents 0 or an integer in the range of 1 to 3, $R^8$ and $R^9$ each independently represent nitro, carboxyl, halogen, $C_1$-$C_6$ alkyl or $C_2$-$C_6$ alkenyl, $m^5$ and $m^6$ each independently represent 0, 1 or 2;

$R^8$ and $R^9$ may be different to each other when $m^5$ and $m^6$ each represent 2, $Y^2$ represents CO or $NR^{10}CO$ wherein $R^{10}$ represents hydrogen or $C_1$-$C_6$ alkyl); and a compound represented by Formula (3); wherein (3)

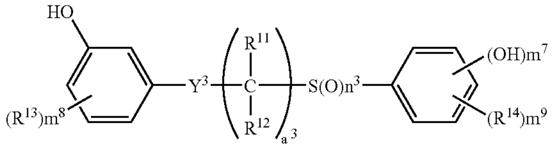

$R^{11}$ and $R^{12}$ each independently represent hydrogen or $C_1$-$C_6$ alkyl, $a^3$ represents an integer of 1 to 6, $n^3$ represents 0, 1 or 2, $m^7$ represents 0 or an integer in the range of 1 to 3, $R^{13}$ and $R^{14}$ each independently represent nitro, carboxyl, halogen, $C_1$-$C_6$ alkyl or $C_2$-$C_6$ alkenyl, $m^8$ and $m^9$ each independently represent 0, 1 or 2;

$R^{13}$ and $R^{14}$ may be different to each other when $m^8$ and $m^9$ each represent 2, $Y^3$ represents CO or $NR^{15}CO$ wherein $R^{15}$ represents hydrogen or $C_1$-$C_6$ alkyl.

5. A recording sheet according to claim 4, wherein the compound represented by Formula (2) and/or the compound represented by Formula (3) each have a content quantity in the range of 5 to 500 parts by weight relative to 100 parts by weight of the compound represented by Formula (1).

6. A composition according to claim 1, further comprising: 4,4'-dihydroxydiphenylsulfone, 4-hydroxy-4'-isopropoxydiphenylsulfone, a diphenylsulfone bridged compound represented by Formula (9) given below;

(9)

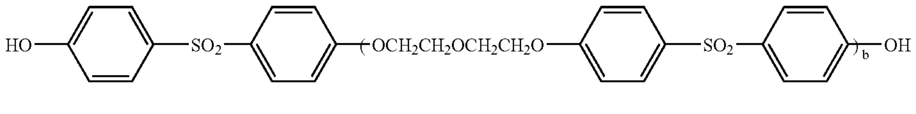

wherein b is an integer of 0 to 6, or mixtures thereof.

wherein (2)

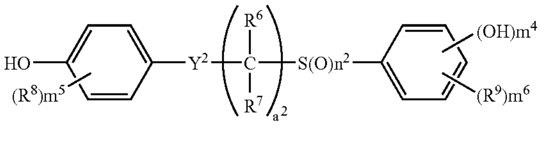

7. A recording material according to claim 2, further comprising:

4,4'-dihydroxydiphenylsulfone, 4-hydroxy-4'-isopropoxydiphenylsulfone, a diphenylsulfone bridged compound represented by Formula (9) given below;

(9)
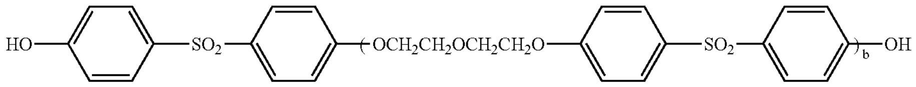
wherein b is an integer of 0 to 6, or mixtures thereof.
* * * * *

UNITED STATES PATENT AND TRADEMARK OFFICE

CERTIFICATE OF CORRECTION

PATENT NO. : 7,390,771 B2
APPLICATION NO. : 10/999630
DATED : June 24, 2008
INVENTOR(S) : Tadashi Kawakami et al.

It is certified that error appears in the above-identified patent and that said Letters Patent is hereby corrected as shown below:

On the title page item (56),

Under Foreign Patent Documents

Insert --JP2001-106364 04/04/01--

Insert --JP2001-244785 08/10/01--

Signed and Sealed this

Ninth Day of September, 2008

JON W. DUDAS
*Director of the United States Patent and Trademark Office*

UNITED STATES PATENT AND TRADEMARK OFFICE

CERTIFICATE OF CORRECTION

PATENT NO. : 7,390,771 B2
APPLICATION NO. : 10/999630
DATED : June 24, 2008
INVENTOR(S) : Tadashi Kawakami et al.

It is certified that error appears in the above-identified patent and that said Letters Patent is hereby corrected as shown below:

On the title page item (63), delete the Related U.S. Application Data and replace it with the following:

--Continuation-in-part of application No. 10/472,125, filed on Sep. 16, 2003, now abandoned, which is a National Stage of PCT/JP02/03159, filed on Mar. 26, 2002, and is a continuation-in-part of application No. PCT/JP03/06818, filed on May 30, 2003.--

Signed and Sealed this

Second Day of December, 2008

JON W. DUDAS
*Director of the United States Patent and Trademark Office*

UNITED STATES PATENT AND TRADEMARK OFFICE

CERTIFICATE OF CORRECTION

PATENT NO. : 7,390,771 B2 
APPLICATION NO. : 10/999630
DATED : June 24, 2008
INVENTOR(S) : Tadashi Kawakami et al.

It is certified that error appears in the above-identified patent and that said Letters Patent is hereby corrected as shown below:

Col. 1, line 10,

Delete "March 26, 2002" and insert --March 29, 2002--.

Signed and Sealed this

Fifth Day of May, 2009

JOHN DOLL
*Acting Director of the United States Patent and Trademark Office*